United States Patent [19]
Tatumoto et al.

[11] Patent Number: 5,897,723
[45] Date of Patent: Apr. 27, 1999

[54] METHOD FOR FABRICATING A CERAMIC COMPOSITE BODY HAVING AT LEAST ONE HOLLOW PORTION THEREIN

[75] Inventors: Hirohiko Tatumoto; Syuichi Nakano, both of Kariya, Japan

[73] Assignee: Nippondenso Co., Ltd., Japan

[21] Appl. No.: 08/683,403

[22] Filed: Jul. 18, 1996

[30] Foreign Application Priority Data

Jul. 18, 1995 [JP] Japan .................................. 7-205156
Jun. 28, 1996 [JP] Japan .................................. 8-188434

[51] Int. Cl.$^6$ ............................ B32B 31/20; G01N 27/26
[52] U.S. Cl. ................................. 156/89.11; 156/89.12; 156/89.16; 156/89.28; 156/245; 204/424; 204/426; 204/429
[58] Field of Search .................................. 156/89, 89.11, 156/89.12, 89.16, 89.28, 245; 264/56, 59, 60, 61, 63, 65, 328.1; 204/421, 424, 425, 426, 428, 429

[56] References Cited

U.S. PATENT DOCUMENTS

| | | | |
|---|---|---|---|
| 3,628,987 | 12/1971 | Nakata et al. | . |
| 4,505,806 | 3/1985 | Yamada | 156/89 X |
| 4,505,807 | 3/1985 | Yamada | 264/61 X |
| 4,585,499 | 4/1986 | Mase et al. | 204/425 X |
| 4,610,741 | 9/1986 | Mase et al. | 156/89 |
| 4,639,305 | 1/1987 | Shibata et al. | 204/424 X |
| 4,670,128 | 6/1987 | Mase et al. | 204/424 X |
| 4,769,123 | 9/1988 | Mase et al. | 204/425 |
| 4,776,943 | 10/1988 | Kitahara | 204/425 X |
| 4,880,519 | 11/1989 | Wang et al. | 204/424 X |
| 4,961,957 | 10/1990 | Kawae et al. | 204/424 X |
| 5,089,071 | 2/1992 | Tominaga et al. | 156/89 |
| 5,169,513 | 12/1992 | Mase et al. | 204/425 X |
| 5,298,147 | 3/1994 | Nakae et al. | 204/425 X |
| 5,384,030 | 1/1995 | Duce et al. | 204/424 X |
| 5,419,827 | 5/1995 | Nanataki et al. | 204/421 |
| 5,421,984 | 6/1995 | Saito et al. | 204/424 X |
| 5,447,618 | 9/1995 | Sugiyama et al. | 204/424 X |
| 5,518,603 | 5/1996 | Furuhashi et al. | 264/61 X |
| 5,522,979 | 6/1996 | Tatumoto et al. | 204/426 X |

FOREIGN PATENT DOCUMENTS

| | | |
|---|---|---|
| 59-29107 | 2/1984 | Japan . |
| 2-238902 | 9/1990 | Japan . |
| 2-50494 | 9/1990 | Japan . |

*Primary Examiner*—Curtis Mayes
*Attorney, Agent, or Firm*—Pillsbury Madison & Sutro, LLP

[57] ABSTRACT

A method of fabricating a sintered ceramic composite body having at last one hollow portion therein is disclosed. According to this method, at least one green ceramic body in the form of a sheet or plate and an adhesive sheet made of a ceramic powder and a binder resin are provided. The adhesive sheet is capable of adhering to the green ceramic body after drying and is shaped to provide a hollow portion in association with green ceramic body. The adhesion body and the green ceramic body are brought into intimate contact with each other so that a hollow portion is established therebetween. The resulting composite body is pressed and sintered to obtain a sintered ceramic composite body having the hollow portion therein. The binder preferably includes acrylic resin(s) and/or vinyl resin(s) having a molecular weight of 300,000 to 800,000 and a glass transition temperature of −30° C. or below.

38 Claims, 7 Drawing Sheets

METHOD FOR FABRICATING A CERAMIC COMPOSITE BODY HAVING AT LEAST ONE HOLLOW PORTION THEREIN

BACKGROUND OF THE INVENTION

1. Field of The Invention

This invention relates to a method for fabricating a ceramic composite body having a laminar structure and at least one hollow portion therein.

2. Description of the Prior Art

FIG. 10 shows a ceramic composite body 9 having a hollow portion 911 therein. For the fabrication of such a hollow ceramic composite body, it is usual to provide ceramic sheets 92, 93 obtained from a ceramic powder and a binder, and an opening-bearing ceramic sheet 91 having an opening 911.

Subsequently, the ceramic sheet 91 is sandwiched between the sheets 92 and 93, and pressed at a compression pressure of 5 MPa to 25 MPa under heating conditions of 70° C. to 160° C. By this, the ceramic sheets 91 to 93 are bonded together to provide a green ceramic body 9.

The green body 9 is sintered to obtain a ceramic composite body having a hollow portion therein as set out in Japanese laid-open Patent Application No. 2-50494.

The binder component or components contained in the ceramic sheets 91 to 93 are softened by the heating. In this condition, the ceramic sheets 91 to 93 are pressed whereupon the respective sheets 91 to 93 are strongly bonded together through the binder component serving as a bonding agent. When the thus obtained green body is sintered, the resultant ceramic composite body 9 is obtained as having little interstices therebetween.

However, the method has the following problem. As stated, the individual ceramic sheets 91 to 93 are softened upon heating, under which a high compression pressure is applied to the sheets. This may undesirably cause great deformation of the ceramic sheets 92, 93 at portions corresponding to the opening 911 of the sheet 91. In the case, the hollow portion 911 may be at least partly closed or deformed. Thus, an undesirably deformed ceramic composite body 9 will be fabricated.

In order to avoid this problem, Japanese Laid-open Patent Application No. 59-29107 proposes the fabrication method which follows.

As shown in FIG. 11, ceramic sheets 91 to 93 are, respectively, provided. Separately, a bonding slurry 98 is provided as having the same composition as that of the ceramic sheets 91 to 93.

The bonding slurry 98 is applied to opposite sides of the ceramic plate 91. Thereafter, the thus applied ceramic plate 91 is sandwiched between the ceramic sheets 92, 93, followed by pressing at a low compression pressure, for example, of about 1 MPa at a low temperature of 30° C. to 50° C.

By this, the ceramic sheets 91 to 93 are bonded together to provide a green composite body 99. The composite body 99 is then sintered to obtain a ceramic composite body having a hollow portion therein.

According to this method, the ceramic sheets 91 to 93 can be laminated at low temperature and low pressure. Accordingly, the ceramic sheets 91 to 93 do not suffer softening or deformation during the course of the pressing.

Nevertheless, the method is disadvantageous in that the ceramic sheet 91 has to be coated with the bonding slurry 98 and dried, so that the fabrication procedure becomes complicated, thus inviting a rise in cost.

Additionally, the coating and drying steps require proper control in viscosity of the slurry 98, the coating thickness, and the drying conditions of the slurry 98 under which the slurry 98 keeps good adhesiveness.

SUMMARY OF THE INVENTION

It is accordingly an object of the invention to provide a method for fabricating a stacked ceramic composite body having at least one hollow portion of high dimensional accuracy therein.

It is another object of the invention to provide a method for fabricating a stacked ceramic composite body by a simple procedure wherein the respective ceramic sheets or bodies are bonded together in an airtight fashion.

The above objects can be achieved, according to one embodiment of the invention, by a method for fabricating a sintered ceramic composite body having at least one hollow portion therein, the method comprising:

providing at least one green ceramic body in the form of a sheet or plate;

further providing an adhesion body which is made of a ceramic powder and a binder resin and is capable of adhesion to the at least one green ceramic body after drying and which is shaped to provide a hollow portion in association with the at least one green ceramic body;

bringing the adhesion body and the at least one green ceramic body into intimate contact with each other so that a hollow portion is established therebetween and pressing the resultant composite body; and sintering the composite body to obtain a sintered ceramic composite body having the hollow portion therein.

The at least one green ceramic body may be in the form of a sheet or plate made according to a doctor blade method. Alternatively, a molded body obtained, for example, by an injection molding method or an extrusion molding method may also be used. Still alternatively, molded bodies obtained by a combination of these methods may be likewise used.

The ceramic materials used for the green ceramic body and the adhesion sheet may be the same as or different from each other provided that they are bonded together during the sintering.

Since the adhesion sheet exhibits good adhesion to the green ceramic body, this sheet is able to adhere to the green ceramic body or bodies under low temperature and low pressure conditions of a temperature of 10 to 50° C. and 1 MPa or below, thereby readily obtaining a green ceramic composite body which is substantially free of any deformation or warpage of a hollow portion contained therein.

This is advantageous in that a high temperature at which the green ceramic body is softened or a high pressure under which the green ceramic body is very liable to deform is not necessary when bringing the adhesion sheet into intimate contact with the at least one green ceramic body. Thus, deformation of the at least one green ceramic body can be prevented upon exertion of pressure thereon. Eventually, this leads to the likelihood that the hollow portion is accurately established without involving any deformation of either the adhesion body or the green ceramic body. The resultant green ceramic composite body keeps its dimensional accuracy.

In a more specific embodiment of the invention, if the adhesion body is recessed or grooved on one side thereof, only one green ceramic body is necessary for forming a composite green body having a hollow portion by placing the green ceramic body on the groove surface of the adhesion body. Alternatively, if the adhesion body has an opening or is in the form of a U shape, the adhesion body is placed between two green ceramic bodies, thereby forming a hollow portion between the two green ceramic bodies. Since the two green ceramic bodies and the intermediate adhesion sheet are strongly bonded together owing to the adhesion of the adhesion sheet under low temperature and low pressure conditions, any failure in airtightness between each of the green ceramic bodies and the adhesion sheet is unlikely to occur. If the resultant green composite body is sintered, layer separation in or deformation of a final body does not take place.

The ceramic materials used as the green ceramic body and the adhesion sheet or body should preferably include alumina, zirconia, mullite, cordierite and the like. These may be used singly or in combination. Especially, if green bodies or other members are made of materials which are different in type from each other, it is preferred to form the adhesion sheet or body from a composition which comprises a plurality of ceramic materials in the form of powders. This is because the coefficient of thermal expansion of the adhesion sheet can be at an intermediate value of different types of ceramics, thus being effective in preventing the breakage of the composite body owing to the thermal stress caused by the difference in the thermal expansion coefficient.

The binders used in the adhesion sheet should preferably be made of at least one resin selected from acrylic resins and vinyl resins which have a molecular weight of 300,000 to 800,000 and a glass transition temperature of −30° C. or below. If the molecular weight is less than 300,000, the adhesion force of the binder resin is not good. Such a resin may not impart good adhesion to the adhesion sheet. On the other hand, if the molecular weight is greater than 800,000, a problem arises in that a ceramic powder is unlikely to be uniformly dispersed and mixed in the binder. When the glass transition temperature exceeds −30° C., the consistency of the binder resin so lowers that good adhesion is not ensured. The lower limit of the glass transition temperature should preferably be −130° C. Lower temperatures are unfavorable because it becomes difficult to keep the shape of body.

Specific and preferred examples of the binder resin include acrylic resins such as polyalkyl methacrylates whose alkyl moiety has from 2 to 10 carbon atoms, polyalkyl acrylates, such as polymethyl acrylate and poly-2-ethylhexyl acrylate, whose alkyl moiety has from 2 to 10 carbon atoms and the like, and vinyl resins such as polyvinyl butyral. The binder resins may be used singly or in combination. These polymers are able to lower the glass transition temperature to a level defined above and can form hydrogen bonds at the interface with an adhered, i.e. the ceramic body, thus ensuring good adhesion.

The ceramic powder and a binder resin used to form the adhesion sheet should preferably be mixed at a ratio by weight of 90:10 to 50:50. This is because if the binder resin is used at a ratio of smaller than 10 relative to 90 of the ceramic powder, the adhesion force becomes undesirably low. In contrast, when the binder resin is used at a ratio of 50 or above, the adhesion sheet obtained after sintering becomes brittle. The ceramic powder should preferably have an average size of from 0.1 to 1 μm.

The adhesion strength between the adhesion sheet and a ceramic body should preferably be in the range of 50 g/25 mm or over when determined according to the method described in JIS Z0237. When the adhesion strength is smaller than 50 g/25 mm, the lamination of the adhesion sheet with or between the ceramic bodies requires high temperature and high pressure conditions of 50° C. or above and 1 MPa or above. This will disable one to obtain a green composite body without deformation of the hollow portion established by the adhesion body in association with the ceramic body or bodies.

The hollow portion in a final ceramic composite body may be a closed or confined one, or may be open to the outside at one side of the composite body. More particularly, if the adhesion sheet has an opening which is not open at any side of the sheet, a closed hollow portion is established on lamination between two ceramic bodies. Alternatively, if the opening is extended to one side of the sheet, e.g. in the form of a U shape, the hollow portion created between the ceramic bodies is open at one side. This is true of the case where the adhesion body is recessed or grooved at one side thereof.

According to another embodiment of the invention, there is also provided a method for fabricating a sintered ceramic composite body having a hollow portion therein which is open to outside at one side thereof, the method comprises the steps of:

providing a green ceramic body in the form of a sheet;

further providing an injection molded body having a recess or groove which is extended to one side thereof, thereby forming a passage when assembled into a ceramic composite body;

providing an adhesion sheet which is made of a ceramic powder and a binder resin and is capable of adhesion to the ceramic body and the injection molded body after drying and which has an opening;

sandwiching the adhesion sheet between the green ceramic body and the injection molded sheet so that the opening of the adhesion sheet is in communication with the passage, and pressing the resultant composite body; and sintering the composite body.

In accordance with this embodiment, the green ceramic body in the form of a sheet and a injection molded block or body, which are usually made of different ceramic compositions having different hardness, can be readily bonded together through the adhesion sheet, thereby forming a hollow portion of high dimensional accuracy in a final ceramic composition body.

In this embodiment, it is preferred that prior to the lamination of the injection molded body with the adhesion sheet, part of the binder component which is present in the injection molded body should be removed by pre-greasing treatment wherein the injection molded body is heated to 600° C. or higher for a time sufficient to achieve a given removal or degreasing rate of the binder component. By the pre-degreasing treatment, the content of the binder resin and the shrinkage rate can be made substantially equal to those of the green ceramic body after the lamination of these bodies. The resultant sintered body becomes substantially free of any layer separation and warpage and ensures good airtightness.

The degreasing or binder-removal rate attained during the course of the pre-treatment should preferably be in the range of 30 to 70 wt % based on the total amount of the binder present at the time of the injection molding.

If the degreasing rate is less than 30 wt %, the resin content and shrinkage rate of the injection molded body become greater than those of the green ceramic body. On sintering, the resultant composite body may suffer layer separation, warpage and a failure in airtightness. On the other hand, when the rate exceeds 70 wt %, the injection molded body considerably lowers in strength, with the attendant problem that the molded body may be broken on stacking with the green body.

The binder-removal rate is calculated according to the equation

Binder-removal rate=[(amount of binder component removed by the pre-treatment)/amount of total binder component)]×100

The sintered ceramic composite body obtained according to the method of the invention has utility in the fields of laminated oxygen sensor devices and A/F sensor devices as used in controlling air-to-fuel ratio in automotive engines.

PREFERRED EMBODIMENTS OF THE INVENTION

Figure 1:
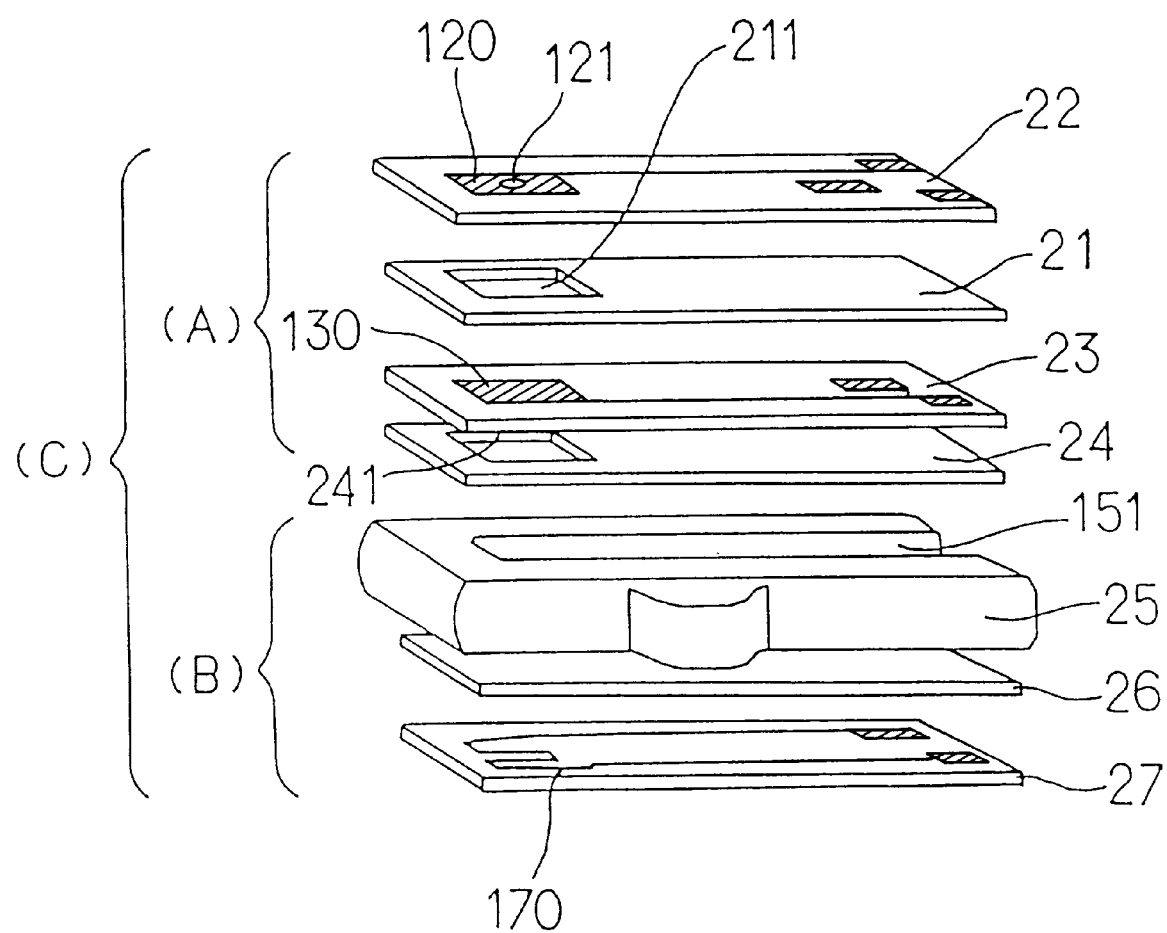
FIG. 1 is a schematic exploded view of a ceramic composite body used in an oxygen sensor device according to one embodiment of the invention.
Figure 2:
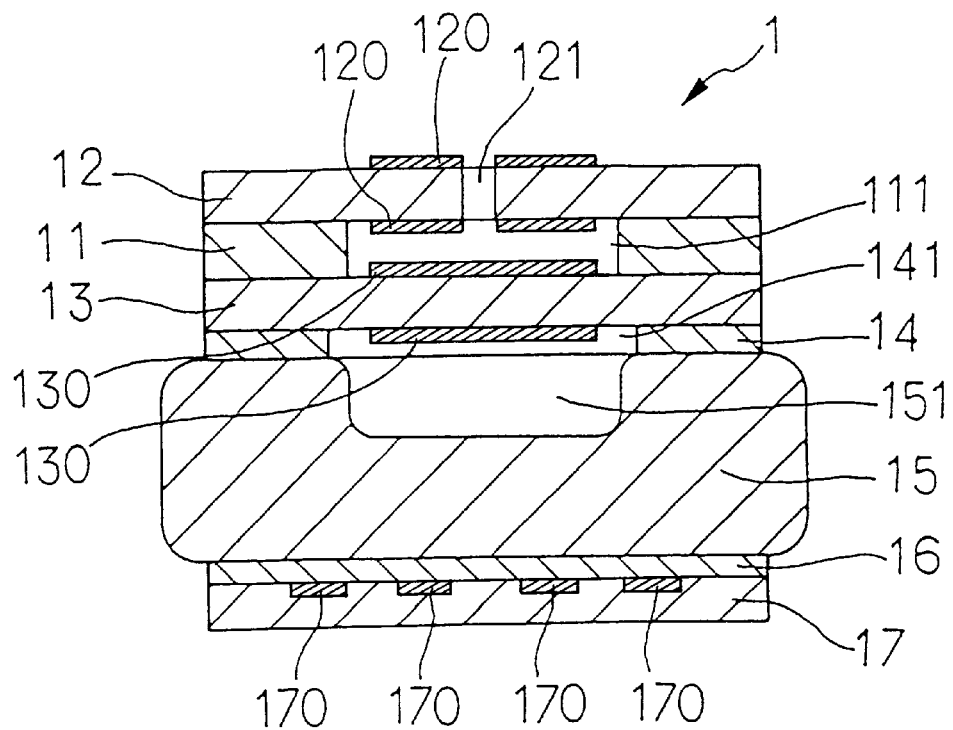
FIG. 2 is a schematic sectional view of the oxygen sensor device shown in FIG. 1.
Figure 3:
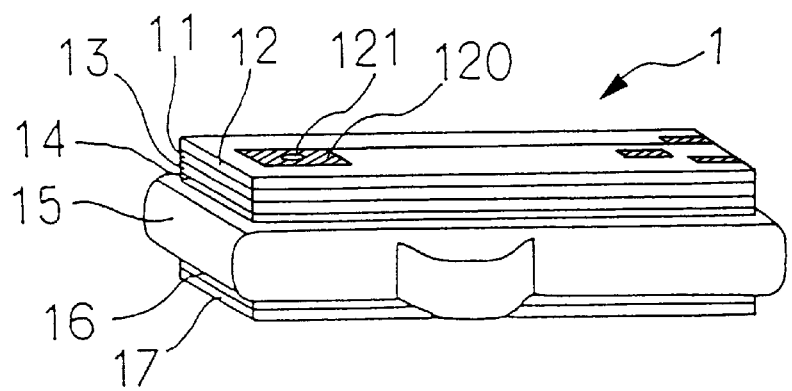
FIG. 3 is a schematic perspective view of the oxygen sensor device of FIG. 1.

Reference is now made to the accompanying figures and particularly, to FIGS. 1 to 3 to illustrate a first embodiment of the invention. In the figures, like reference numerals indicate like parts or members unless otherwise indicated.

In this embodiment, the ceramic composite body is applied to the fabrication of an oxygen sensor device having a laminar or stacked structure.

As is particularly shown in FIG. 1, for the fabrication of a stacked ceramic composite body having a hollow portion therein, green ceramic bodies 22, 23 each in the form of a sheet or plate are first provided. The ceramic bodies 22, 23 are made of a ceramic powder and a binder resin. Examples of the ceramic powder are those as defined before. Examples of the binder resin may be those defined with respect to the adhesion body. Other binder resins ordinarily used for these purposes may also be employed. The ceramic body is usually made of a composition comprising 70 to 97 wt % of a ceramic powder and 3 to 30 wt % of a binder resin. As a matter of course, additives such as dispersants, plasticizers and the like may be used by a usual manner.

Separately, an adhesion sheet 21 having an opening 211 is provided. The adhesion sheet 21 is made of a composition comprising a ceramic powder and a binder preferably at a mixing ratio by weight of 90:10 to 50:50 as defined before and should have a predetermined adhesion strength when determined by the method described in JIS Z 0237. The opening 211 defines a hollow portion when the adhesion sheet 21 is brought into intimate contact with the ceramic bodies 22, 23.

These bodies 22, 23 and the adhesion sheet 21 are, respectively, prepared from slurries in organic solvents for binders resins by a doctor blade method or the like and provided after drying.

The adhesion sheet 21 is then sandwiched between and brought into intimate contact with the green ceramic bodies 22, 23 and pressed under conditions of a temperature of 10 to 50° C. and a low pressure of about 1 MPa or below. Due to the presence of the binder resin in the adhesion sheet 21, the sheet 21 and the ceramic bodies 22, 23 are strongly bonded together under mild conditions to provide a green composite body. This body is sintered by a usual manner under conditions of a temperature of from 1300 to 1600° C.

The application of the sintered ceramic body set out above to a stacked oxygen sensor device is described.

As shown in FIGS. 2 and 3, a stacked oxygen sensor device 1 includes a pump cell 12, a sheet 11 for forming a chamber of a gas to be measured, an electrochemical cell 13, a reference gas passage-forming plate 15, and a heater unit 17 stacked in this order as is particularly shown in FIG. 2. An adhesive layer 14 is provided between the electrochemical cell 13 and the reference gas passage-forming plate 15. Likewise, an adhesive layer 16 is provided between the reference gas passage-forming plate 15 and the heat unit 17.

The pump cell 12 has a pair of electrodes 120 on opposite side thereof and a pinhole 121 from which a gas to be measured is introduced, as shown in FIG. 2. The electrochemical cell 13 also has a pair of electrodes 130 formed on opposite sides thereof. The pump cell 12 and the electrochemical cell 13 are, respectively, formed of the ceramic bodies 22, 23 shown in FIG. 1.

The measuring gas chamber-forming sheet 11 has an opening 111 which serves as a measuring gas chamber in association with the pump cell 12 and the electrochemical cell 13 as shown in FIG. 2. This sheet 11 corresponds to the opening-bearing adhesion sheet 21, and the measuring gas chamber 111 is formed with the aid of the opening 211 in FIG. 1.

The reference gas passage-forming plate 15 has a reference gas passage 151 as recessed. A reference gas chamber 141 is formed between the electrochemical cell 13 and the plate 15 correspondingly to the thickness of the adhesive layer 14. The heater unit 17 has a heat pattern 170 capable of generating heat by application of an electric current.

The fabrication method of the sensor is more particularly described by way of example.

EXAMPLE 1

Green ceramic sheets 22, 23 which are, respectively, used as the pump cell 12 and the electrochemical cell 13 are made in the following manner.

100 parts by weight (hereinafter referred to simply as "parts") of a zirconia powder having an average particle size of 0.6 µm, to which 5 wt % of a yttria powder is added, 3.5 parts of polyvinyl butyral binder, 8.2 parts of dibutyl phthalate plasticizer and 1.0 part of sorbitan trioleate dispersant are dissolved and dispersed in 26.8 parts of a mixed solvent of ethanol and toluene, thereby obtaining a slurry.

A zirconia sheet is formed from the slurry according to a doctor blade method in a thickness of about 5 mm. After drying, two zirconia sheets are, respectively, screen printed to form electrodes 120,130 on the respective sheets, thereby obtaining ceramic sheets 22, 23. The ceramic sheet 22 is formed with a pinhole 121 through the electrode 120.

Separately, the adhesion sheet 21 used as the measuring gas chamber-forming sheet 11 is made in the following manner.

100 parts of a zirconia powder having an average particle size of 0.6 µm, to which 5 wt % of yttria is added, 23.9 parts of polyalkyl methacrylate binder, 4.8 parts of dibutyl phthalate plasticizer, and 4.2 parts of polycarboxylic acid dispersant are dissolved and dispersed in 49.9 parts of a mixed solvent of ethanol and toluene to obtain a slurry. The ratio of the ceramic powder and the binder in the sheet 21 is about 4.18 (100/23.9).

A 100 µm thick zirconia sheet is formed by a doctor blade method using the slurry. Thereafter, the zirconia sheet is dried and punched to form the opening 211 to obtain an intermediate sheet 21.

Moreover, sheets 24, 26 as shown in FIG. 1 are, respectively, made in the following manner. These sheets 24, 26, respectively, serve as the adhesive layers 14, 16 in FIG. 2.

100 parts of alumina powder having an average particle size of 0.3 µm, 35.9 parts of polyalkyl methacrylate binder, 7.2 parts of dibutyl phthalate plasticizer, and 6.3 parts of polycarboxylic acid dispersant are dissolved and dispersed in 74.9 parts of a mixed solvent of ethanol and toluene to obtain a slurry.

A 50 µm thick alumina sheet is formed according to a doctor blade method using the slurry. Thereafter, the alumina sheet is dried to provide the sheet 26. When the alumina sheet which has been dried is punched with a mold die to form an opening 241, the sheet 24 is obtained.

A sheet 27 which serves as the heater unit 17 is made in the following manner.

100 parts of an alumina powder having an average particle size of 0.3 µm, 7 parts of polyvinyl butyral binder, 11 parts of dibutyl phthalate plasticizer, and 6 parts of polycarboxylic acid dispersant are dissolved and dispersed in 64 arts of a mixed solvent of ethanol and toluene to obtain a slurry.

An alumina sheet is formed according to a doctor blade method using the slurry. Then, a heat pattern 170 is screen printed on the alumina sheet to obtain a sheet 27.

An alumina molding 25 serving as the reference gas passage-forming plate 15 is made in the following manner.

100 parts of an alumina powder having an average particle size of 0.3 µm is mixed with 19 parts of a mixed binder of paraffin wax, styrene-butadiene rubber, acrylic resin, vinyl acetate polymer and stearic acid. The resultant mixture is injection molded into a desired shape, followed by preliminary degreasing treatment at a de-greasing rate of 50 wt % to obtain an alumina molded body 25.

The ceramic sheet 22, adhesion sheet 21, ceramic body 23, sheet 24, alumina molded body 25, sheet 26, and heating unit 27 are stacked in a manner as shown in FIG. 1.

Initially, the adhesion sheet 21 is sandwiched between the ceramic sheets 22, 23, followed by pressing at a compression pressure of 1 MPa at a temperature of 20° C. to obtain a green composite body (A) shown in FIG. 1.

Separately, the sheet 26 is sandwiched between the alumina molded body 25 and the sheet 27 and pressed at a compression pressure of 1 MPa to obtain a green composite body (B).

Subsequently, the sheet 24 is sandwiched between the alumina molded body 25 of the green composite body (B) and the ceramic sheet 23 of the green composite body (A), followed by pressing at a compression pressure of 1 MPa to provide a green composite body (C) shown in FIG. 1.

Finally, the body (C) is de-greased at approximately 600° C. and sintered at a temperature of 1500° C. for 2 hours to obtain a stacked oxygen sensor device 1.

The opening-bearing sheet 21 of the green composite body (A) was subjected to measurement of adhesion strength according to an adhesion strength evaluation method (i.e. 180° peeling-off method) based on JIS 0237, revealing that the strength was 500 g/25 mm.

Likewise, the sheets 24 and 26 of the green composite bodies (B) and (C) were measured with respect to the adhesion strength, both having an adhesion strength of 800 g/25 mm.

The method of evaluation of the adhesion strength based on the method described in JIS Z -0237 is described with reference to FIGS. 12A, 12B, 12C and 12D.

Figure 12A:
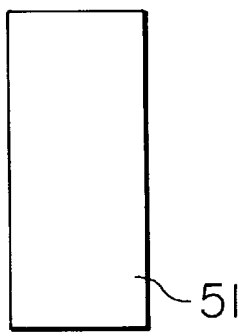
FIGS. 12A, 12B, 12C and 12D are, respectively, schematic illustrative views illustrating a method of evaluating an adhesion force according to the method described in JIS Z 0237.

As shown in FIG. 12A, a rectangular sample piece 51 having a size of 30 mm×80 mm is first made using a ceramic composition to be measured.

A stainless steel sheet 52 (SUS 304) having a thickness of 1.5 to 2.0 mm, a width of about 50 mm and a length of about 150 mm is provided. A wet abrasive paper (#280) is wound about a roller having a ball core and reciprocated along the length of the stainless steel sheet 52 ten times to polish the surface of the stainless steel sheet 52.

After the polishing, the stainless steel sheet 52 is wiped with toluene-soaked cloth until the surface is stain-free. The thus wiped sheet 52 is dried by allowing it to stand.

The test piece 51 is placed on the stainless steel sheet 52, whereupon no force is applied to the sheet 52 but the piece 51 is merely placed thereon. The placement is made gently without introduction of any bubbles at the interface.

Figure 12B:
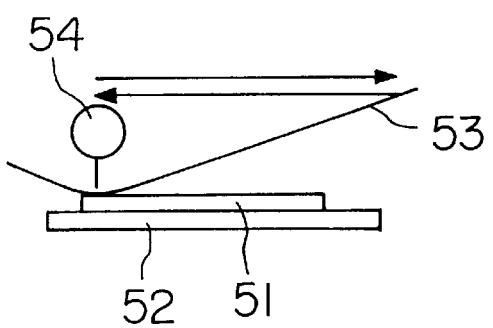

A 25 mm wide Damblon tape 53 (#3200) is pressed against the test piece 51. Upon the pressing, a roller 54 having a weight of 2 kg is rolled over the Damblon tape 53 along the arrows (both directions) as shown in FIG. 12B and the tape 53 is pressed. The pressing speed is 300 mm/minute.

Figure 12C:
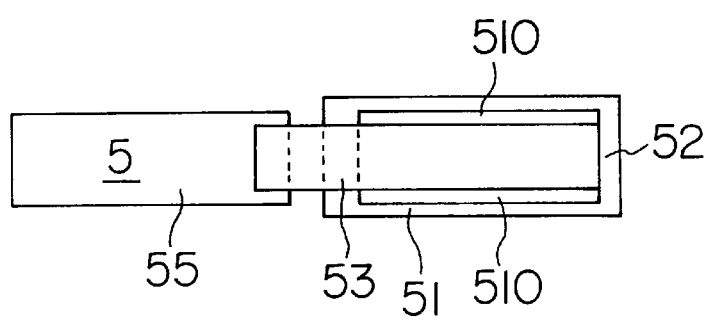
Figure 12D:
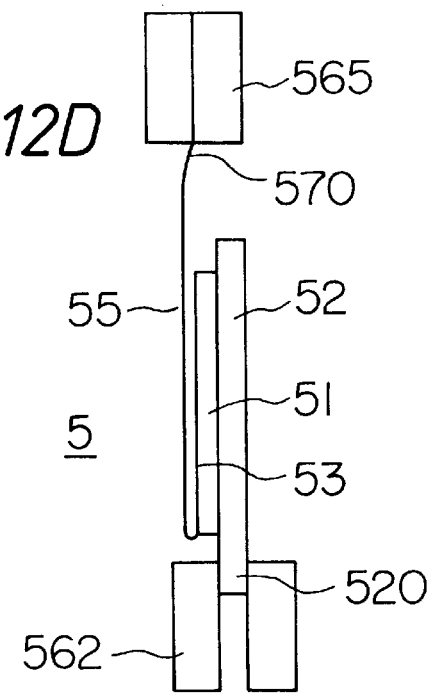

A rectangular paper sheet 55 with a size of 30 mm×190 mm is adhered to the Damblon tape 53 at the tip portion thereof as shown in FIG. 12C.

The additional portions 510 of the test piece 51 which are not covered with the Damblon tape 53 are removed to make the test piece 51 and the Damblon tape 53 uniform at the widths thereof. This is particularly shown in FIG. 12C. It will be noted that if the tackiness of the test piece 51 is too strong to remove the additional portions from the stainless steel sheet 52, the test piece 51 may be only cut in conformity with the width of the Damblon tape 53 by means of a cutter.

By this, a sample piece 5 used to evaluate the adhesion strength is obtained.

The paper sheet 55 is then enfolded at 180°. Moreover, the test piece 51 is partly peeled off from the stainless steel sheet 52 along with the Damblon tape 53. The length of the peeled-off portion is 25 mm.

The paper sheet 55 and the stainless steel sheet 52 are, respectively, fixedly held with chucks 565, 562 at ends 570 and 520.

The chuck 565 is pulled up along the direction of arrow at a rate of 300 mm/minute to peel off the test piece 51 from the stainless steel sheet 52.

The force required for the peeling is measured and determined as adhesion strength.

The observation of the stacked oxygen sensor device 1 reveals that no deformation took place in the reference gas passage 151, reference gas chamber 141 and measuring gas chamber 111 and that any failure in airtightness between adjacent layers was not found in the device.

In the method for fabricating the ceramic composite body according to this embodiment of the invention, the adhesion sheet 21 has relatively high adhesiveness. This sheet adheres to the ceramic sheets 22, 23 under low temperature and low pressure conditions to obtain a green composite body. Accordingly, the green bodies 22, 23 are prevented from softening or deforming at the time of the stacking or lamination. This, in turn, leads to the unlikelihood that the hollow portion created between the sheets 22, 23 on the lamination is broken or deformed. Thus, the final sintered ceramic composite body ensures the hollow portion of high dimensional accuracy.

The adhesiveness of the sheet 21 permits the ceramic sheets 22, 23 and the adhesion sheet 21 to be bonded strongly, so that any failure in airtightness between the sheets 22, 23 and the sheet 21 is not caused, or any layer separation does not take place. In addition, the ceramic composite body obtained after sintering does not suffer any deformation or warpage.

The ceramic composite body illustrated in this embodiment is the laminar oxygen sensor device 1. In this device 1, the electrode 120 formed on the pump cell 12 and the electrode 130 formed on the electrochemical cell 13 are facing each other in the measuring gas chamber 111. In this state, if the measuring gas chamber 111 is at least partly closed or deformed, short-circuiting between the electrodes 120 and 130 may take place. This will result in the sensor device 1 which is poor in oxygen concentration detecting function.

Moreover, where layer separation takes place or where airtightness between the adjacent layers is not good, the function of detecting an oxygen concentration with the sensor device also becomes poor.

In this connection, the ceramic composite body obtained by the method according to the embodiment of the invention has a hollow portion, i.e. the measuring gas chamber 111, which is not deformed at all during the course of the fabrication. This leads to the fabrication of a stacked oxygen sensor device which ensures good performance.

The adhesion sheet 21 does not lose its adhesiveness after drying. This does not require any wet/dry control in the fabrication procedure. Hence, the method of the invention is simple with a reduced number of control parameters and is thus trouble-saving, resulting in low fabrication costs.

In the above embodiment, the adhesion sheet has an opening in the form of a rectangle. Accordingly, a closed hollow portion is established when the adhesion sheet is sandwiched between two green ceramic sheets. This opening may be extended to one end of the adhesion sheet. In the case, the hollow portion is open to the outside on sandwiching. Moreover, the adhesion sheet may have a groove or recess in a desired form in place of the opening. In the case, only one green ceramic body placed on the adhesion sheet is sufficient to make a composite ceramic body having a hollow portion therein. The groove or recess may be confined or may be extended to one end of the adhesion sheet.

Another embodiment of the invention is described with reference to FIGS. 4 and 5. The ceramic composite body obtained in this embodiment has an opening-bearing adhesion sheet and a recessed adhesion sheet, both of which exhibit good adhesion at normal temperatures after drying. The ceramic composite body of this embodiment is applicable as a stacked oxygen sensor device, like the first embodiment of FIG. 1.

Figure 4:
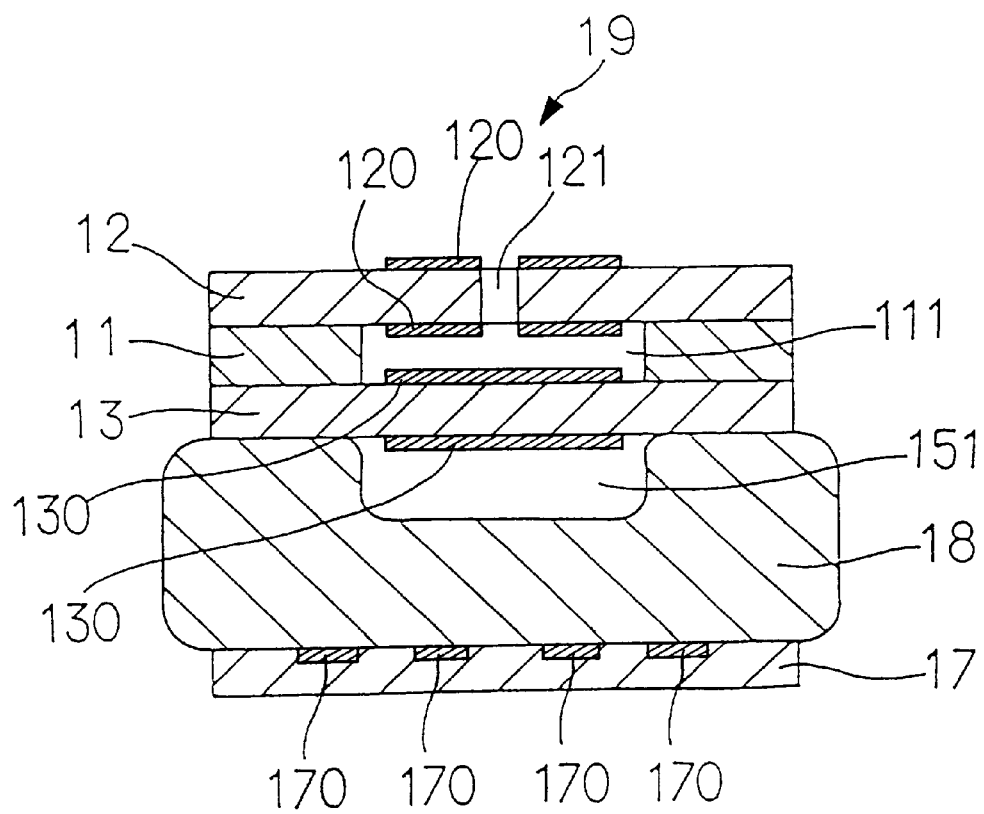
FIG. 4 is a schematic sectional view of an oxygen sensor device using a ceramic composite body according to another embodiment of the invention.

FIG. 4 shows a stacked oxygen sensor device 19. The device 19 includes a pump cell 12, a measuring gas chamber-forming plate 11, an electrochemical cell 13, a reference gas chamber-forming plate 18 and a heater unit 17.

Figure 5A:
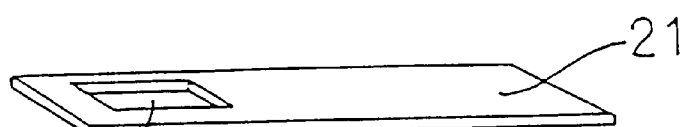
FIGS. 5A and 5B are, respectively, schematic illustrative views of an adhesion sheet and a recessed body used in the embodiment shown in FIG. 4.
Figure 5B:
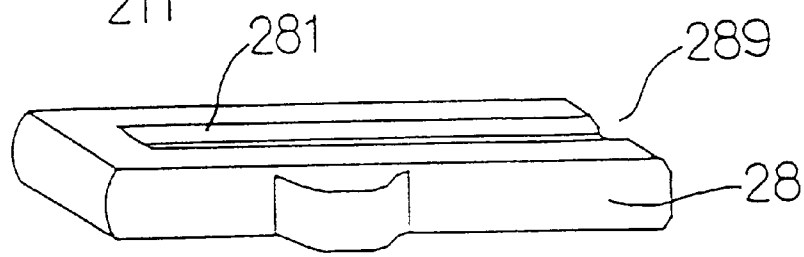

As shown in FIG. 5, the measuring gas chamber forming plate 11 is made of an adhesion sheet 21, and the reference gas chamber-forming plate 18 is made of a recessed adhesion body 28 having an elongated recess 281.

The fabrication of the stacked oxygen sensor device 19 is described.

Ceramic sheets used as the pump cell 12 and the electrochemical cell 13, a sheet used as the heater unit 17, and the opening-bearing adhesion sheet 21 used as the measuring gas-forming plate 11 are, respectively, formed substantially in the same manner as in the first embodiment and in Example 1.

Then, the recessed adhesion body 28 used as the reference gas chamber-forming plate 18 is formed as follows. A mixed composition as used for the adhesion sheet 21 is prepared and injection molded in a desired shape. The resultant body 28 exhibits adhesiveness.

The recessed adhesion body 28 has a recess or groove 281 open, as 289, to the outside when assembled as the stacked oxygen sensor device 19. More particularly, the opening 289 serves as an inlet for a reference gas. As a matter of course, the recess or groove 281 has a bottom and thus is not an opening, like the opening of the sheet 21.

The adhesion sheet 21 is sandwiched between two ceramic sheets as in the first embodiment to obtain a composite body. Then, the recessed adhesion body 28 is sandwiched between the composite body and the heater unit sheet 17 to obtain a green composite body. The binder in the composite body is removed to a predetermined level by heating in air. The resultant composite body is sintered under conditions similar to those of the first embodiment to obtain the stacked oxygen sensor device 19.

In this embodiment, two adhesion bodies 21 and 28 are used. If the body 28 is used in combination with one ceramic green sheet or body, like the cell 13 in FIG. 4, a composite body having a hollow portion, open at one end, can be readily obtained.

Similar results and effects as in the first embodiment are obtained in this case.

A further embodiment of the invention is described with reference to FIGS. 6, 7A and 7B. This embodiment is directed to a ceramic composite body which includes two adhesion sheets. The ceramic composite body is illustrated as being applied as a stacked oxygen sensor device as in the foregoing embodiments.

Figure 6:
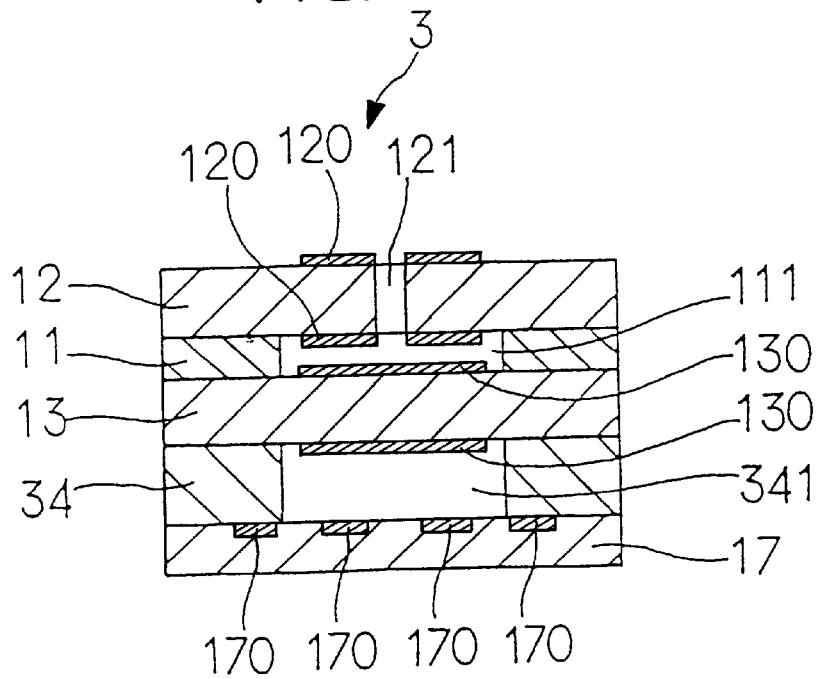
FIG. 6 is a schematic sectional view of an oxygen sensor device made of a ceramic composite body according to a further embodiment of invention.

FIG. 6 shows a stacked oxygen sensor device 3 including a pump cell 12, a measuring gas chamber-forming plate 11, an electrochemical cell 13, a reference gas chamber-forming plate 34 and a heater unit 17.

Figure 7A:
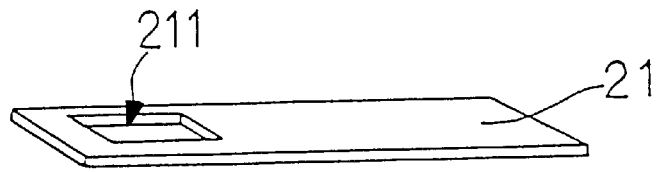
FIGS. 7A and 7B are, respectively, schematic illustrative views of adhesion sheets having different types of openings therein in the embodiment shown in FIG. 6.
Figure 7B:
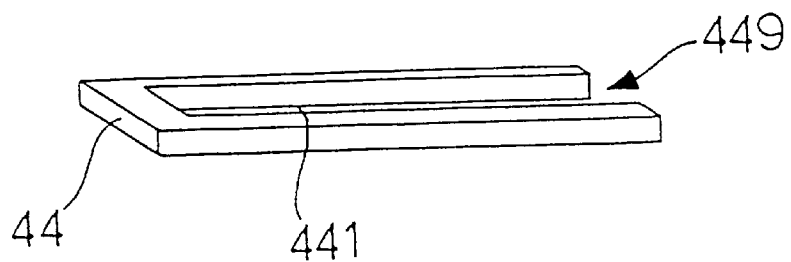

As shown in FIGS. 7A and 7B, the measuring gas chamber-forming plate is made of an adhesion sheet 21 having an opening 211, and the reference gas chamber-forming plate 34 is made of an adhesion sheet 44.

The fabrication of the stacked oxygen sensor device 3 is more particularly described in the following Example 2.

EXAMPLE 2

Green ceramic sheets used as the pump cell 12 and the electrochemical cell 13 are, respectively, made in the same manner as in Example 1.

Then, adhesion sheets 21, 44 used as the measuring gas chamber-forming plate 11 and the reference gas chamber-forming plate 34 are, respectively, made in the following manner.

100 parts of an alumina powder having an average size of 0.3 $\mu$m, 35.9 parts of polyalkyl methacrylate binder, 7.2 parts of dibutyl phthalate plasticizer, and 6.3 parts of polycarboxylic acid dispersant are dissolved and dispersed in 74.9 parts of a mixed solvent of ethanol and toluene to obtain a slurry.

100 $\mu$m thick alumina sheets are formed from the slurry by a doctor blade method. These alumina sheets are dried at a temperature of 70° C. and punched by means of the respective dies corresponding to openings 211, 441 to obtain adhesion sheets 21, 44.

The sheet 44 has the opening 441 in the form of a U shape, so that the opening 441 is open, as 449, at one end when assembled into a final body wherein the opening 441 constitutes a passage open to the outside. Accordingly, the open end 449 serves as an inlet for a reference gas in the final stacked oxygen sensor device 3.

The ratio by weight of the ceramic powder and the binder in the sheets 21, 44 is about 2.79 (100/35.9).

Subsequently, a sheet used as the heater unit 17 is made in the following manner.

100 parts of an alumina powder having an average size of 0.3 $\mu$m, 7 parts of polyvinyl butyral binder, 11 parts of dibutyl phthalate plasticizer, and 6 parts of polycarboxylic acid dispersant are dissolved and dispersed in 64 parts of a mixed solvent of ethanol and toluene to obtain a slurry.

An alumina sheet is formed by a doctor blade method using the slurry, followed by drying and screen printing a heat pattern to obtain the sheet 17.

The adhesion sheet 21 is sandwiched between two ceramic sheets and pressed at a compression pressure of 1 MPa to obtain a composite body.

Further, the sheet 44 is sandwiched between the green composite body and the sheet 17 and pressed at a compression pressure of 1 MPa to obtain a green composite body.

The green composite body is degresed and sintered at a temperature of 1450° C. to obtain a stacked oxygen sensor device.

The adhesion sheets 21, 44 of the green composite body were, respectively, subjected to measurement of adhesion strength in the same manner as in Example 1, both having an adhesion strength of about 800 g/25 mm.

Visual observation of the stacked oxygen sensor device revealed that the reference gas chamber 341 and the measuring gas chamber 111 both suffered no deformation and that the airtightness between the adjacent sheets or layers was good.

A still further embodiment of the invention is described with reference to FIGS. 8, 9A and 9B wherein one adhesion sheet is sandwiched between two ceramic sheets. The resultant ceramic composite body is applicable as a stacked oxygen sensor device as in the foregoing embodiments.

Figure 8:
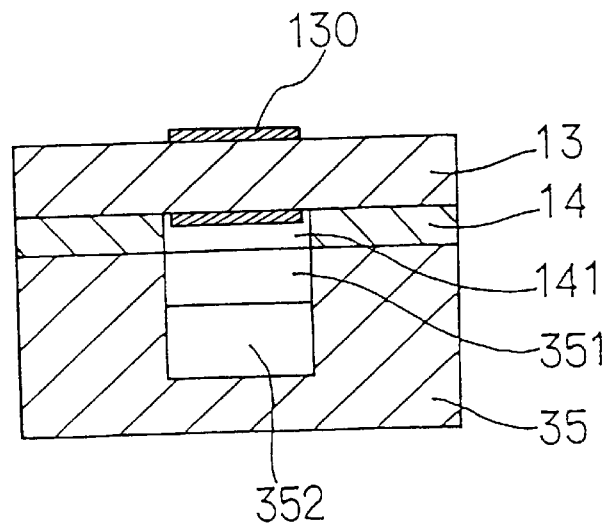
FIG. 8 is a schematic sectional view of an oxygen sensor device made of a ceramic composite body according to a still further embodiment of the invention.
Figure 9A:
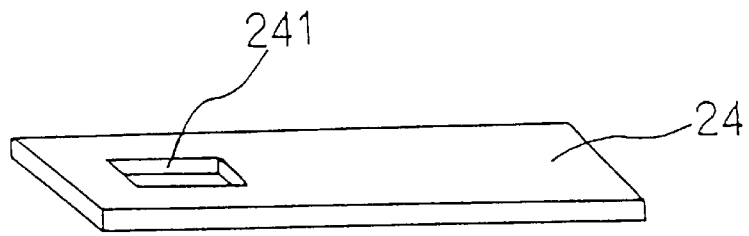
FIGS. 9A and 9B are, respectively, schematic illustrative views of an adhesion sheet and an injection molded body used in the embodiment shown in FIG. 8.

The stacked oxygen sensor device of FIG. 8 has a structure wherein any heater unit is not integrally combined, but has an electrochemical cell 13, a reference gas chamber-forming sheet 14 and a reference gas passage-forming body 35. The reference gas chamber-forming sheet 14 has an opening 241, as shown in FIG. 9A, to establish a reference gas chamber 141, i.e. the plate 14 is made of an adhesion sheet 24 shown in FIG. 9A.

Figure 9B:
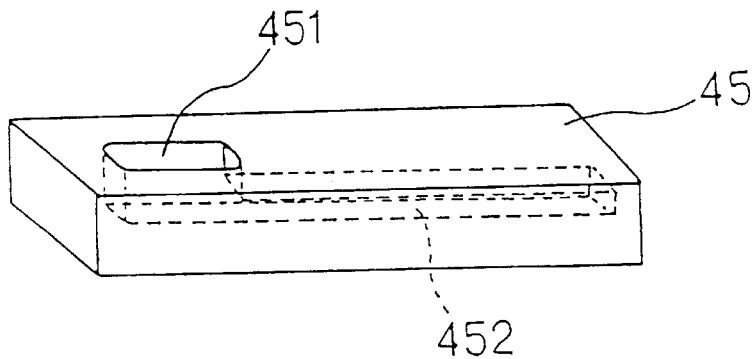
Figure 10:
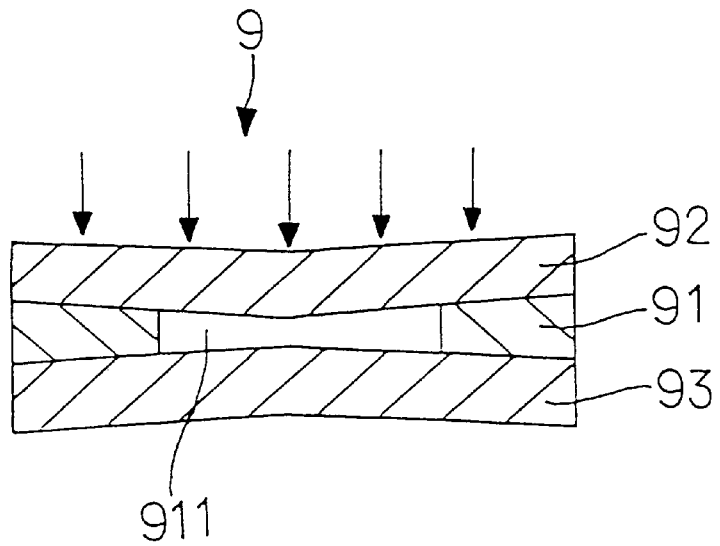
FIG. 10 is an illustrative view of a known ceramic laminar body for illustrating the problem thereof.
Figure 11:
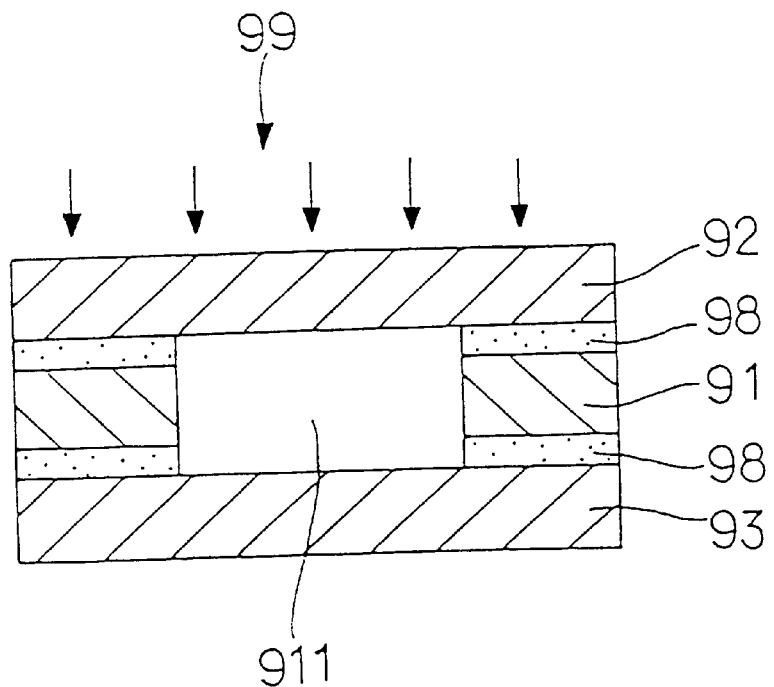
FIG. 11 is an illustrative view of another type of known ceramic laminar body for illustrating the problem thereof.

The reference gas passage-forming body 35 is made of an alumina molding 45, which has a reference gas passage 452 within the molding 45 as shown in FIG. 9B and an opening 451 communicating with the reference gas chamber 141 of FIG. 8.

The fabrication of the ceramic composite body of this embodiment is more particularly described in the following example.

EXAMPLE 3

A ceramic body for the electrochemical cell 13 is formed in the same manner as in Example 1.

The adhesion sheet 24 is then made in the following manner.

100 parts of an alumina powder having an average size of 0.3 $\mu$m, 35.9 parts of polyalkyl methacrylate, 7.2 parts of dibutyl phthalate plasticizer, and 6.3 parts of polycarboxylic acid dispersant are dissolved and dispersed in 74.9 parts of a mixed solvent of ethanol and toluene to obtain a slurry.

An alumina sheet is formed by a doctor blade method using the slurry, followed by drying and punching by a mold die to form the opening 241, thereby obtain the sheet 24. The ratio of the ceramic powder and the binder in the sheet 21 is about 2.79 (=100/35.9).

The alumina molded body 45 serving as the reference gas passage-forming body 35 is made in the following manner.

100 parts of an alumina powder having an average particle size of 0.3 $\mu$m is mixed with 19 parts of a mixed binder of paraffin wax, styrene-butadiene rubber, acrylic resin, vinyl acetate polymer and stearic acid. The resultant mixture is injection molded into a desired shape, followed by preliminary de-greasing treatment at a de-greasing rate of 50 wt % to obtain an alumina molded body 45.

The ceramic body 23, adhesion sheet 24 and alumina molded body 45 are stacked in a manner as shown in FIG. 8 and pressed at a compression pressure of 1 MPa to obtain a green composite body. Finally, the thus obtained green composite body is de-greased at 600° C. and sintered at a temperature of 1500° to obtain a stacked oxygen sensor device.

The device has characteristic features as in that of Example 1.

It should be noted here that when the injection molded body is in direct contact with the adhesion sheet, this body should preferably be made of a ceramic composition which comprises 50 to 90 wt % of a ceramic powder and 10 to 50 wt % of a binder component. The ceramic powders may be those defined before. The binder components include waxes such as paraffin wax, or the like, rubbers such as styrene-butadiene rubbers, or acrylic or vinyl acetate resins. Besides, higher fatty acids such as stearic acid may be added to the binder system.

What is claimed is:

1. A method for fabricating a sintered ceramic composite body having at least one hollow portion therein, the method comprising:

providing two green ceramic bodies in the form of a sheet or plate;

further providing a green sheet having an opening therein, said green sheet being made of a ceramic powder and a binder resin and capable of self-adhesion to said two green ceramic bodies when sandwiched between said two green ceramic bodies after drying, wherein said binder is at least one member selected from the group consisting of acrylic resins and vinyl resins which have a molecular weight of 300,000 to 800,000 and a glass transition temperature of −30° C. or below;

sandwiching said green sheet between said two green ceramic bodies so that a hollow portion is established only by the opening of said green sheet and pressing the resultant composite body; and sintering the composite body to obtain a sintered ceramic body having the hollow portion therein.

2. A method according to claim 1, wherein said hollow portion is confined.

3. A method according to claim 1, wherein said hollow portion is open to outside at one end thereof.

4. A method according to claim 1, wherein said ceramic powder is a member selected from the group consisting of alumina, zirconia, mullite and cordierite.

5. A method according to claim 1, wherein said binder is at least one member selected from polyalkyl methacrylates and acrylates, and polyvinyl butyral.

6. A method according to claim 1, wherein a ratio by weight of the ceramic powder and the binder in said adhesion sheet is in the range of 90:10 to 50:50.

7. A method according to claim 1, wherein an adhesion force of said adhesion sheet is 50 g/25 mm when determined according to a method wherein said adhesion sheet is pressed against a stain-free SUS 304 sheet by rolling a roller having a weight of 2 kg over said adhesion sheet at a pressing speed of 300 mm/minute, is cut into a 25 mm wide pieces, and is peeled off from the SUS 304 sheet at a rate of 300 mm/minute by a 180° peel-off test.

8. A method according to claim 1, wherein said resultant composite body is pressed at a compression pressure as low as 1 Mpa or below.

9. A method for fabricating a sintered ceramic composite body having at least one hollow portion therein, the method comprising:

providing at least one green ceramic body in the form of a sheet or plate;

further providing an adhesion sheet which is made of a ceramic powder and a binder resin and is capable of adhesion to the at least one green ceramic body after drying and which is shaped to provide a hollow portion in association with the at least one green ceramic body, wherein said binder is at least one member selected from the group consisting of acrylic resins and vinyl resins which have a molecular weight of 300,000 to 800,000 and a glass transition temperature of −30° C. or below;

bringing the adhesion sheet and the at least one green ceramic body into intimate contact with each other so that a hollow portion is established therebetween and pressing the resultant composite body; and sintering the composite body to obtain a sintered ceramic composite body having the hollow portion therein, wherein said adhesion sheet has a groove on one side thereof and is stacked with a green ceramic body on a grooved side.

10. A method according to claim 9, wherein said groove is confined when said adhesion sheet is stacked with said green ceramic body.

11. A method according to claim 9, wherein said groove is open to outside at one end thereof when said adhesion sheet is stacked with said green ceramic body.

12. A method according to claim 9, wherein said ceramic powder is a member selected from the group consisting of alumina, zirconia, mullite and cordierite.

13. A method according to claim 9, wherein said binder is at least one member selected from polyalkyl methacrylates and acrylates, and polyvinyl butyral.

14. A method according to claim 9, wherein a ratio by weight of the ceramic powder and the binder in said adhesion sheet is in the range of 90:10 to 50:50.

15. A method according to claim 9, wherein an adhesion force of said adhesion sheet is at least 50 g/25 mm when determined according to a method wherein said adhesion sheet is pressed against a stain-free SUS 304 sheet by rolling a roller having a weight of 2 kg over said adhesion sheet at a pressing speed of 300 mm/minute, is cut into a 25 mm wide piece, and is peeled off from the SUS 304 sheet at a rate of 300 mm/minute by a 180° peel-off test.

16. A method for fabricating a sintered ceramic composite body having a hollow portion therein, the method comprising:

providing at least one green ceramic body in the form of a sheet or plate;

further providing at least one adhesion sheet which is made of a dispersion composition of a ceramic powder in at least one binder resin selected from the group consisting of acrylic resins and vinyl resins at a mixing ratio by weight of 90:10 to 50:50, said at least one adhesion sheet being shaped to provide a hollow portion in association with the at least one green ceramic body, wherein said acrylic resins and vinyl resins have a molecular weight of 300,000 to 800,000 and a glass transition temperature of −30° C. or below;

stacking the at least one adhesion sheet with said at least one ceramic body and pressing the resultant composite body at a pressure of 1 MPa or below; and sintering the pressed composite body to obtain the sintered ceramic composite body having a hollow portion therein, wherein said at least one adhesion sheet consists of an adhesion sheet having a recess and stacked at a recessed side thereof with a green ceramic body.

17. A method according to claim 16, wherein said at least one green ceramic body consists of two green ceramic bodies, and wherein said adhesion sheet is sandwiched between said two green ceramic bodies.

18. A method according to claim 16, wherein said is confined when said adhesion sheet has been sandwiched.

19. A method according to claim 17, wherein said recess is extended to one end of said adhesion sheet.

20. A method according to claim 16, wherein said at least one resin consists of the acrylic resin selected from the group consisting of polyalkyl acrylates and methacrylates.

21. A method according to claim 16, wherein said at least one resin consists of polyvinyl butyral.

22. A method according to claim 16, further comprising:

providing an injection molded body;

providing two green ceramic bodies sandwiching therebetween an adhesion sheet;

stacking said injection molded body with one of said two green ceramic bodies provided at a low position thereof at the first-mentioned stacking step, said injection molded body having a groove in the form of a U shape open to outside when stacked and being made of such a dispersion composition as of said adhesion sheet.

23. A method for fabricating a sintered ceramic composite body having a hollow portion therein which is open to outside at one side thereof, the method comprising the steps of:

providing a green ceramic body in the form of a sheet;

further providing an injection molded green body having a passage which is formed therein and extends to one side thereof;

providing a green sheet having an opening capable of communication with the passage, said green sheet being made of a ceramic powder and a binder resin and capable of adhesion to the two green ceramic body and the injection molded body after drying, wherein said binder is at least one member selected from the group consisting of acrylic resins and vinyl resins which have a molecular weight of 300,000 to 800,000 and a glass transition temperature of −30° C. or below;

sandwiching said green sheet between said green ceramic body and said injection molded sheet so that the opening of said sheet is in communication with the passage, and pressing the resultant composite body; and sintering the composite body.

24. A method according to claim 23, wherein said ceramic powder is a member selected from the group consisting of alumina, zirconia, mullite and cordierite.

25. A method according to claim 23, wherein said binder is at least one member selected from the group consisting of polyalkyl methacrylates and acrylate, and polyvinyl butyral.

26. A method according to claim 23, wherein a ratio by weight of the ceramic powder and the binder in said adhesion sheet is in the range of 90:10 to 50:50.

27. A method according to claim 23, wherein an adhesion strength of said adhesion sheet is at least 50 g/25 mm when determined according to a method wherein said adhesion sheet is pressed against a stain-free SUS 304 sheet by rolling a roller having a weight of 2 kg over said adhesion sheet at a pressing speed of 300 mm/minute, is cut into a 25 mm wide piece, and is peeled off from the SUS 304 sheet at a rate of 300 mm/minute by a 180° peel-off test.

28. A method according to claim 23, wherein said injection molded body is preliminary degreased prior to the stacking with said adhesion sheet to remove part of said binder therefrom.

29. A method according to claim 28, wherein said binder is removed in an amount of 30 to 70 wt % based on the total amount of the binder present in said injection molded body.

30. A method according to claim 23, wherein said resultant composite body is pressed at a compression pressure as low as 1 MPa or below.

31. A method for fabricating an oxygen sensor which comprises:

providing a pump cell made of a green solid electrolyte in the form of a sheet or plate and a pair of electrodes formed on opposite sides of said green solid electolyte;

providing an electrochemical cell made of a green solid electrolyte in the form of a sheet or plate and a pair of electrodes formed on opposite sides of the second-mentioned green solid electrolyte;

further providing an opening-bearing sheet which is made of a dispersion composition of a ceramic powder in at least one binder resin selected form the group consisting of acrylic resins and vinyl resins at a mixing ratio by weigh of 90:10 and 50:50 and which has an opening capable of establishing a hollow portion in association with both cells, wherein said at least one resin binder has a molecular weight of 300,000 to 800,000 and a glass transition temperature of −30° C. or below;

stacking said electrochemical cell and said pump cell via said opening-bearing sheet and pressing the resultant composition body; and sintering the composition body to obtain a sintered body consisting of said pump cell, said electrochemical cell and said opening-bearing sheet and having the hollow portion therein.

32. A method according to claim 31, further comprising a reference gas passage-forming plate stacked with said electrochemical cell and having a recess opened to the outside so as to establish a passage for a reference gas when assembled into a composite body, said reference gas passage-forming plate being made of an injection molded body.

33. A method according to claim 32, wherein said injection molded body is preliminary degreased prior to the stacking with said sheet to remove part of said binder therefrom.

34. A method according to claim 33, wherein said binder is removed in an amount of 30 to 70 wt % based on the total amount of the binder present in said injection molded body.

35. A method according to claim 31, wherein said ceramic powder is a member selected from the group consisting of alumina, zirconia, mullite and cordierite.

36. A method according to claim 31, wherein said binder is at least one member selected from the group consisting of polyalkyl methacrylates and acrylate, and polyvinyl butyral.

37. A method according to claim 31, wherein an adhesion strength of said sheet is at least 50 g/25 mm when determined according to a method wherein said sheet is pressed against a stain-free SUS 304 sheet by rolling a roller having a weight of 2 kg over said sheet at a pressing speed of 300 mm/minute, is cut into a 25 mm wide piece, and is peeled off from the SUS 304 sheet at a rate of 300 mm/minute by a 180° peel-off test.

38. A method according to claim 31, wherein said resultant composite body is pressed at a compression pressure as low as 1 MPa or below.

* * * * *